United States Patent [19]

Fujikura et al.

[11] 4,025,568

[45] May 24, 1977

[54] 4-HOMOISOTWISTYL BROMIDE

[75] Inventors: Yoshiaki Fujikura; Yoshiaki Inamoto; Hiroshi Ikeda; Naotake Takaishi, all of Wakayama, Japan

[73] Assignee: Kao Soap Co., Ltd., Tokyo, Japan

[22] Filed: Dec. 18, 1975

[21] Appl. No.: 641,895

[30] Foreign Application Priority Data

Dec. 23, 1974 Japan .......................... 49-147807

[52] U.S. Cl. .................. 260/648 R; 260/666 PY; 260/561 R; 260/563 P; 424/325
[51] Int. Cl.² ........................................ C07C 23/20
[58] Field of Search ............................. 260/648 R

[56] References Cited

UNITED STATES PATENTS 3,845,124  10/1974  Deslongchamps ............. 260/617 F

*Primary Examiner*—D. Horwitz
*Attorney, Agent, or Firm*—Woodhams, Blanchard and Flynn

[57] ABSTRACT

4-homoisotwistyl bromide has biological activities to plants. It is useful as an intermediate to produce 3-acetylamino-4-homoisotwistane which has an antiviral effect and a biological activity to plants. 4-homoisotwistyl bromide is obtained by reacting 4-homoisotwistane with liquid bromine.

2 Claims, No Drawings

4-HOMOISOTWISTYL BROMIDE

BACKGROUND OF INVENTION

FIELD OF INVENTION

This invention relates to a compound of formula (II) given below, 4-homoisotwistyl bromide (tricyclo[5.3.1.0$^{3,8}$]undecyl 3-bromide).

More specifically, the invention relates to a process for the preparation of 4-homoisotwistyl 3-bromide of formula (II) characterized by reacting 4-homoisotwistane (tricyclo[5.3.1.0$^{3,8}$]undecane) of formula (I) given below with liquid bromine to brominate the 3-position (or the 7-position) of the starting compound. This reaction is represented by the following reaction scheme:

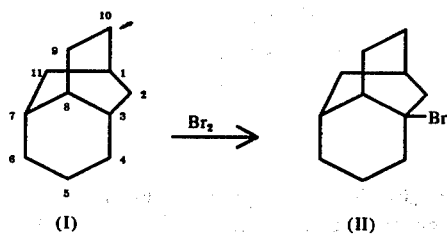

SUMMARY OF INVENTION

4-Homoisotwistane is a tricyclic cage hydrocarbon which was recently discovered, and its properties or functions have hardly been known and only a few derivatives synthesized by us are known.

The derivative of the present invention (4-homoisotwistyl bromide) has biological activities to plants and is valuable as a compound for anti-viral agents or a drug modifier and other various chemicals. Further, it is important as a starting substance of lubricant additives, extreme pressure agents, rust-preventive agents, fiber oiling agents and other agents that can be derived therefrom.

It is a primary object of the present invention to obtain 4-homoisotwistyl bromide (II) with ease. This object can be attained by reacting 4-homoisotwistane (I) with liquid bromine. This synthesis process has recently applied to synthesis of adamantanes by Osawa et al [Osawa et al, Terahedron Lett., 115 (1974)], and it is known that this process is valuable for the synthesis of bromine derivatives of adamantanes. However, it is quite impossible to predict what position or how many positions will be brominated when this bromination process is applied to 4-homoisotwistane (I), because 4-homoisotwistane (I) is a tricyclic hydrocarbon compound and its reactivity has not been studied at all. As a result of our research works, we found that this bromination reaction occurs selectively on the 3-position (or the 7-position) of 4-homoisotwistane (I) and only one bromine atom is introduced into this position. Based on this finding, the present inventors have now completed this invention. The product bromide (II) was confirmed to be a mono-brominated compound based on the elementary analysis and mass spectrum analysis. The fact that the bromide (II) retains the skeleton of the compound (I) can be confirmed by the fact that when the compound (II) is reduced with metallic lithium in t-butyl alcohol, the compound (I) is obtained quantitatively.

Further, in the NMR spectrum of the compound, no $^1$H signal assignable to a proton geminal to bromine atom was obtained. Accordingly, it is concluded that bromine is bonded to the tertiary carbon atom but not to the secondary carbon atom. Still further, the $^{13}$C-NMR spectrum shows 11 signals, and hence, it is seen that the skeleton has 11 carbon atoms in the different environment. Therefore, as described above, the bromine atom is substituted at the 3- or 7-position.

In practising the process of the present invention, the reaction is sufficiently advanced by mixing 4-homoisotwistane (I) with liquid bromine and stirring the mixture. An equivalent amount of bromine may be used for this reaction, but in view of the fact that the reaction rate is very low at room temperature, it is generally preferred that bromine be used in an amount of 5 to 10 moles per mole of the starting compound (I). If this reaction is conducted in the presence of an organic solvent such as carbon tetrachloride, chloroform, dichloromethane, trichloroethane or the like, the reaction is hardly advanced. Therefore, it is not preferred to conduct this bromination reaction in the presence of a solvent. The reaction temperature is generally within a range of from $-20°$ C. to $+58°$ C. In a pressure vessel, the reaction may be accomplished at a higher temperature of up to $+100°$ C. In general, however, good results are obtained when the reaction is carried out at room temperature.

The process of this invention will now be illustrated in detail by reference to the following Examples.

EXAMPLE 1

3.0 g (20 millimoles) of 4-homoisotwistane (I) was added to 10 ml (194 millimoles) of liquid bromine, and the mixture was stirred at room temperature for 10 minutes.

The reaction mixture was gradually added under agitation to a saturated aqueous solution of sodium bisulfite to remove excess bromine. The resulting aqueous solution was extracted two times with 20 ml of carbon tetrachloride, and the extract was dried on magnesium sulfate. Carbon tetrachloride was removed by distillation and the oily residue was purified by sublimation to give 1.66 g of a white crystal (yield: 35%).

Melting Point:
  59.5° C.

Elementary Analysis Values as $C_{11}H_{17}Br$:
  Found: C = 57.1%, H = 7.5%, Br = 34.2%
  Calculated: C = 57.68%, H = 7.48%, Br = 34.87%

IR Spectrum (Nujol, cm$^{-1}$):
  1201, 1110, 1050, 940, 890, 840, 750

NMR Spectrum (CCl$_4$ solvent, TMS internal standard, δ):
  2.6 – 1.0 (multiplet)

Mass Spectrum m/l (relative intensity):
  230 (0.2, M_), 228 (0.3, M_), 150 (23),
  149 (100), 107 (18), 94 (22), 93 (21),
  91 (25), 81 (27), 79 (37), 67 (40)

Referential Example 1

Reduction of 4-Homoisotwistyl-3-Bromide to 4-Homosiotwistane:

0.34 g (1.42 millimoles) of 4-homoisotwistyl-3-bromide (II), 0.3 g (4.05 millimoles) of t-butyl alcohol, 3 ml of THF and 0.15 g (21.6 millimoles) of metallic lithium were stirred for 3 hours under reflux.

The reaction mixture was cooled, and 5 ml of methanol was added thereto and the mixture was agitated for a while. Then, the mixture was poured in 20 ml of water and extracted three times with n-pentane. The extract was dried on anhydrous magnesium sulfate and the solvent was distilled off to give 0.16 g of a crystal (the yield being 82%). By comparison of the results of chromatographical analysis and infrared absorption spectrum analysis of the product with that of authentic specimen, this compound was identified as 4-homoisotwistane.

4-homoisotwistyl bromide of this invention is useful as an intermediate to 3-acetylamino-4-homoisotwistane (3-acetylamino-tricyclo-[5.3.1.0$^{3,8}$]-undercane). 3-acetylamino-4-homoisotwistane (III) is obtained by reacting 4-homoisotwistyl bromide with acetonitrile in the presence of sulfuric acid. In this reaction, the concentration of sulfuric acid to be used is in the range between 20% and 100%, preferably 85% and 98%. The reaction temperature is from -20° to 90° C., preferably from 5° to 50° C. 3-acetylamino-4-homoisotwistane obtained by the reaction is considered to have an antiviral effect and a biological activity to plants. Furthermore, it is suitable for lubricant additives, extreme pressure agents, rust-preventive agents, fiber oiling agents and other agents.

EXAMPLE 2

While a mixture of 5.30 g (0.022 mol) of 3-bromo-4-homoisotwistane and 40 ml of acetonitrile was stirred at a room temperature, 100 ml of 95 percent sulfuric acid was added dropwise to the mixture over about 30 minutes. After the addition finished, the mixture was subjected to reaction at a room temperature for further 20 hours. Then, the reaction mixture was poured into 200 ml of ice water and it was extracted twice with 100 ml of ethyl ether. The ether portion thereof was washed with 100 ml of water and was dried on anhydrous sodium sulfate. Subsequently, the ether portion was subjected to filtration and concentration. The objective product was obtained with recrystallization from ethyl ether. It was colorless crystal. The yield was 83 percent (3.8 g). The melting point was 125 to 126° C. in a sealed tube.

Elementary Anaylsis Values as $C_{13}H_{21}NO$:
Found: C = 75.1%, H = 9.9%, N = 6.6%
Calculated: C = 75.3%, H = 10.2%, N = 6.7%
IR Spectrum (nujol, cm$^{-1}$):
3300 ($\nu$ N—H), 1640 ($\nu$ C=O), 1540 ($\delta$ N—H), 1310, 740

NMR Spectrum (CCl$_4$ solvent, TMS internal standard, $\delta$):
2.1 - 1.0 (complicated multiplet), 2.2 (singlet,

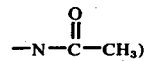
)

Mass Spectrum, m/l (relative intensity)
207 (M$^+$, 42), 148 (100), 136 (25), 119 (21), 94 (41),
91 (17), 79 (19), 60 (36), 43 (19), 18 (19)

3-acetylamino-4-homoisotwistane is useful as an intermediate to 3-amino-4homoisotwistane or its acid salt, which is represented by the following formula:

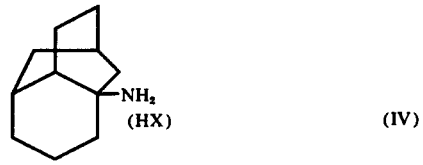

in which HX is an organic or inorganic acid. The amino-compound is obtained by hydrolysis of 3-acetylamino-4-homoisotwistane. The acid moiety of the acid salt thereof includes organic or inorganic acids, for example, hydrochloric acid, sulfuric acid, thiosulfuric acid, paratoluene sulfonic acid, phosphoric acid, citric acid and oxalic acid.

The compound (IV) has been found to have particularly good effects against Newcastle disease virus among Paramyxo virus belonging to RNA type on monolayer culture of thick embryo fibroblasts. Moreover, it does not give the cell poisonous character. It is the fact that the compound (IV) can prevent the multiplication of virus at about one tenth concentration of that of adamantylamine hydrochloride which is well known as an anti-influenza virus agent.

What we claim is:
1. 4-homoisotwistyl-3-bromide.
2. A process for preparing 4-homoisotwistyl-3-bromide, which comprises stirring a mixture of (A) 4-homoisotwistane and (B) liquid bromine, at a molar ratio of A/B of from 1/5 to 1/10, at a temperature of from −20° C to +100° C, under a pressure effective to maintain (B) in the liquid state, the reaction being carried out in the absence of a solvent, and recovering 4-homoisotwistyl-3-bromide from the reaction mixture.

* * * * *